United States Patent
Liu et al.

(10) Patent No.: US 12,123,028 B2
(45) Date of Patent: Oct. 22, 2024

(54) VIRAL INACTIVATION METHODS FOR CONTINUOUS MANUFACTURING OF ANTIBODIES

(71) Applicant: Bayer HealthCare LLC, Whippany, NJ (US)

(72) Inventors: Shengjiang Liu, Lafayette, CA (US); June Xiaojun Zou, Richmond, CA (US); Janice Hsiu Mei Lee, Hayward, CA (US)

(73) Assignee: Bayer HealthCare LLC, Whippany, NJ (US)

( * ) Notice: Subject to any disclaimer, the term of this patent is extended or adjusted under 35 U.S.C. 154(b) by 749 days.

(21) Appl. No.: 17/292,652

(22) PCT Filed: Nov. 14, 2019

(86) PCT No.: PCT/US2019/061436
§ 371 (c)(1),
(2) Date: May 10, 2021

(87) PCT Pub. No.: WO2020/102505
PCT Pub. Date: May 22, 2020

(65) Prior Publication Data
US 2022/0002679 A1    Jan. 6, 2022

Related U.S. Application Data

(60) Provisional application No. 62/767,652, filed on Nov. 15, 2018.

(51) Int. Cl.
*C12N 7/00* (2006.01)

(52) U.S. Cl.
CPC ...... *C12N 7/00* (2013.01); *C12N 2740/13063* (2013.01)

(58) Field of Classification Search
None
See application file for complete search history.

(56) References Cited

U.S. PATENT DOCUMENTS

| 5,639,730 A | 6/1997 | Eibl et al. |
| 2016/0333046 A1 | 11/2016 | Fisher et al. |

FOREIGN PATENT DOCUMENTS

| EP | 1161958 A1 | 12/2001 | | |
| WO | WO-9413329 A1 * | 6/1994 | ............ | A61K 35/14 |
| WO | WO-2012014183 A1 * | 2/2012 | ............ | C07K 1/165 |
| WO | 2013010797 A1 | 1/2013 | | |
| WO | 2014004103 A1 | 1/2014 | | |
| WO | 2014025771 A2 | 2/2014 | | |
| WO | WO-2015073633 A1 * | 5/2015 | ............ | A61K 38/00 |
| WO | WO-2015158776 A1 * | 10/2015 | ............ | A61L 2/0082 |
| WO | WO-2016207328 A1 * | 12/2016 | ............ | C07K 1/18 |

OTHER PUBLICATIONS

Burczyk; et al, "Synthesis and Surface Properties of N-Alkyl-N-methylgluconamides and N-Alkyl-N-methyllactobionamides", Journal of Colloid and Interface Science, 2001, vol. 240, 552-558.
Dichtelmueller; et al, "Effective Virus Inactivation and Removal by Steps of Biotest Pharmaceuticals IGIV Production Process", Results in Immunology, 2012, vol. 2, 19-24.
Floyd; et al, "Viral Aggregation: Effects of Salts on the Aggregation of Poliovirus and Reovirus at Low pH", Applied and Environmental Microbiology, Jun. 1978, vol. 35 No. 6, 1084-1094.
Foley; et al., "Derivation and synthesis of Renewable Surfactants", Chemical Society Reviews, Feb. 21, 2012, vol. 41 No. 4, 1405-1608.
Gaudin; et al, "Low-pH Conformational Changes of Rabies Virus Glycoprotein and Their Role in Membrane Fusion", Journal of Virology, 1993, vol. 63 No. 3, 1365-1372.
Horowitz; et al, "Annex 4: Guidelines on viral inactivation and removal procedures intended to assure the viral safety of human blood plasma products", WHO Techical Report, Nov. 19, 2004, Series No. 924.
"International Preliminary Report on Patentability for corresponding application PCT/US2019/061436 mailed May 27, 2021".
KEmpf; et al, "Pathogen Inactivation and Removal Procedures Used in the Production of Intravenous Immunoglobulins", Biologicals, Mar. 2007, vol. 35 No. 1, 35-42.
Klutz; et al, "Continuous Viral Inactivation at Low pH Value in Antibody Manufacturing", Chemical Engineering and Processing, 2016, vol. 102, 88-101.
Madsen; et al, "Biodegradability and aquatic toxicity of glycoside surfactants and a nonionic alcohol ethoxylate", Journal of the American Oil Chemists Society, vol. 73, 929-933.
Pamphilon; Derwood, "Viral Inactivation of Fresh Frozen Plasma", British Journal of Heamatology, Jun. 2000, vol. 109 No. 4, 680-693.
Scott; et al, "Incativation of Enveloped Viruses: Seeking Alternatives to a Problematic Surfactant", BioProcess International eBook Series, 2018.
Stalmans; et al, "The Environmental Properties of Glucose Amide—A New Nonionic Surfactant", SOFW-Journal, 1993, 794-806.
Szymanski; et al, "Determination of Non-ionic Surfactants and their Biotransformation by-products Adsorbed on Alive Activated Sludge", Water Research, 2003, 281-288.
Traczyk; et al, "Efficency of Non-Ionic Surfactant Removal in Biological Sewage Treatment Plants", Polish J. of Environ. Stud., 2005, vol. 15 No. 3, 493-499.

(Continued)

*Primary Examiner* — Benjamin P Blumel
*Assistant Examiner* — Jeffrey Mark Sifford
(74) *Attorney, Agent, or Firm* — Timothy H. Joyce

(57) ABSTRACT

This disclosure relates to methods for use in inactivating viruses. The virus inactivation methods are for use in continuous process manufacturing of a biologic such as an antibody, and include separating an eluate using a column, subjecting said eluate to an orthogonal treatment of low pH and detergent simultaneously wherein, the time for viral inactivation is reduced. In addition, the detergent can be added to buffer system in purification process to achieve the same effect. The biologic in each treatment case is retained.

11 Claims, 8 Drawing Sheets

(56) References Cited

OTHER PUBLICATIONS

"Singapore Search Report and Written Opinion from corresponding SG application No. 11202103790W dated Dec. 24, 2022".
International Search Report on Patentability of International Application No. PCT/US2019/061436 mailed Mar. 9, 2020.

* cited by examiner

VIRAL INACTIVATION METHODS FOR CONTINUOUS MANUFACTURING OF ANTIBODIES

BACKGROUND

The present embodiments relate to a method for viral inactivation during continuous manufacturing of biological products, in particular, antibody-based therapeutic products.

Manufacturers are required by regulatory agencies to demonstrate that their production processes have the capacity to clear infectious viruses by removal and/or inactivation of viral contaminants that may be present in their biotherapeutic products. Inactivation of either endogenous or exogenous adventitious enveloped viruses by low pH treatment is commonly implemented in manufacturing processes as it is simple, low cost and robust. Low pH viral inactivation is typically carried out on the pooled eluate collected from a protein affinity capture column, and the low pH condition is achieved by the titration of a weak acid to the pooled eluate. However, not all antibodies are very stable under this low pH condition and would form aggregates, thus the treatment has to be carried out at a higher pH range. As a result, viral inactivation becomes less robust and a longer treatment time is needed to achieve the same log reduction of viral infectivity.

Other than low pH viral inactivation, affinity column chromatography, anion exchange chromatography and viral filtration are commonly employed as viral removal steps in the manufacturing of antibodies. Both anion exchange chromatography and viral filtration have been shown to be very effective in the removal of both enveloped and non-enveloped viruses. Unlike anion exchange chromatography and viral filtration, however, the effectiveness of protein A affinity in removal of viruses is very limited. As such, it is desirable to eliminate the protein A affinity chromatography as a validated viral clearance step and replace it with a simpler and more robust viral inactivation step.

Detergents have been previously employed for viral inactivation in the manufacturing process of biologics. Addition of detergents to the clarified cell culture supernatant is often employed to inactivate enveloped viruses while antibodies are labile to the low pH treatment though traditionally solvent or detergent. Triton X-100 has been shown to be very effective and robust in inactivation of enveloped viruses. Generic conditions for inactivation of enveloped viruses by Triton X-100 have also been employed. However, octlyphenol, a degradation product of Triton x-100, is an endocrine disruptor that can harm humans, fish, and other organisms, thus adversely impacting the environment. Moreover, the defined limits for octylphenol discharge are 0.01 to 0.1 parts per billion (ppb), which would be very costly for biologics manufacturers to remove from bioprocess waste streams.

There is an increasing interest in the biopharmaceutical industry to move from operating in batch mode to continuous manufacturing in order to meet the future requirements of the biopharmaceutical industry. A manufacturing process is considered a fully continuous process if it is composed of integrated (physically connected) continuous unit operation with zero or minimal hold volume in between. Currently, almost all unit operations of standard antibody manufacturing are in the continuous processing ready mode except for the low pH viral inactivation step that is currently carried out in a batch process. In general, the eluate pool of the protein A affinity column capture step is adjusted to the desired pH by the titration of a weak acid to the pooled protein A eluate and held in a vessel or a bag for the required inactivation time of 60-120 minutes. Although an effective low pH viral inactivation of $\geq 5.0$ logs reduction of retrovirus could be achieved under the conditions of pH$\leq 3.6$, at room temperature, for an incubation time $\geq 30$ minutes (ASTM, 2012), not all monoclonal antibodies are very stable under this low pH condition and would form aggregates. Therefore, viral inactivation treatments have to be carried out at a higher pH (e.g. 3.7 to 3.9). Generally, the higher the pH and the longer inactivation time needed, the higher the product loss due to the aggregation of antibodies, which represents a challenge in adapting to continuous process. Therefore, the challenge is to convert low pH viral inactivation in batch mode to continuous process while ensuring the viral inactivation time in the flow mode is as precisely controlled as it is in the batch mode.

To accommodate the typical residence time (1-2 hr) for low pH viral inactivation and flow eluates, a long and narrow pipe is needed for developing a unit operation for continuous low pH viral inactivation. However, such a unit operation would generate high back pressure and a wide residence time distribution, resulting in a longer residence time for antibody molecules close to the tube walls. This can cause a drastic decrease of monomers in favor of the formation of antibody aggregates due to an infinitely long residence time for low pH treatment. Currently, a "coiled-flow inverter" (CFI) consisting of helix modules and 90 degree bends with a narrow residence time has been proposed to address these problems. What is needed is a more precise treatment system with a narrow residence time distribution for the operation of continuous viral inactivation. These and other issues have been addressed by the present embodiments.

SUMMARY

The embodiments comprise methods used for viral inactivation in continuous manufacturing of biologics. The methods comprise separating an eluate with a biologic and active virus using a column, subjecting the eluate with an active virus to an orthogonal treatment of low pH and a non-ionic detergent simultaneously to inactivate the virus wherein the time for viral inactivation of the eluate is reduced as compared to the treatment time of the eluate using low pH or the non-ionic detergent separately and the biologic is retained.

BRIEF DESCRIPTION OF THE DRAWINGS

The skilled artisan will understand that the drawings, described below, are for illustration purposes only. The drawings are not intended to limit the scope of the present teachings or claims in any way.

shows X-MuLV inactivation kinetics and LRF achieved during 30 minutes of incubation in a sample of mAb1 protein A eluate at pH 3.91; the line in (—△—) shows X-MuLV inactivation kinetics and LRF achieved during 30 minutes of incubation in a sample of mAb1 protein A eluate at pH 3.91 and at the presence of 0.1% of Mega-10.

Figure 3:
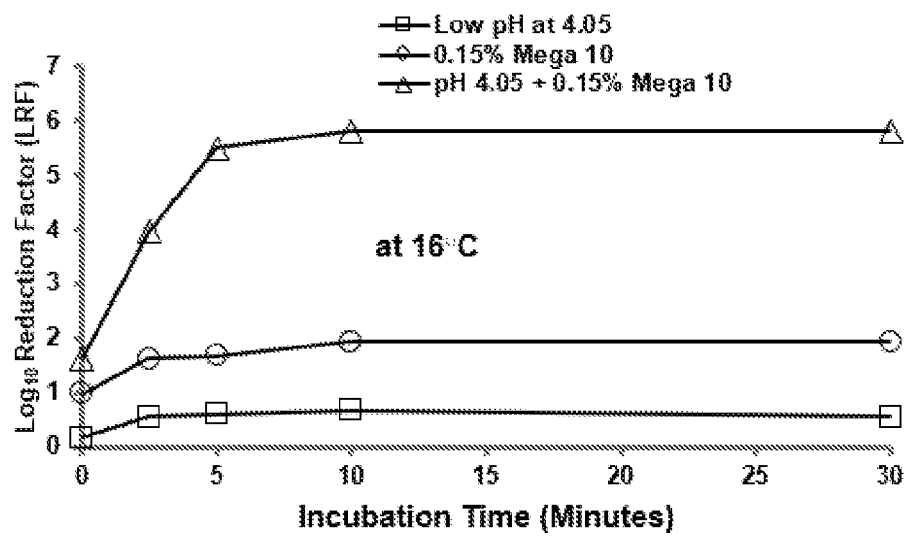

FIG. 3 shows the synergistic effects of dual treatment with low pH and Mega-10 on reducing X-MuLV infectivity after incubation at 16° C. in a sample of mAb2 protein A eluate. The line in (—⊖—) shows X-MuLV inactivation kinetics and LRF achieved during 30 minutes of incubation with 0.15% of Mega-10; the line in (—□—) shows X-MuLV inactivation kinetics and LRF achieved during 30 minutes of incubation in a sample of mAb2 protein A eluate at pH 4.05; the line in (—△—) shows X-MuLV inactivation kinetics and LRF achieved during 30 minutes of incubation in a sample of mAb2 protein A eluate at pH 4.05 and at the presence of 0.15% of Mega-10.

FIG. 4 shows the synergistic effects of dual treatment with low pH and Mega-10 on reducing time needed to inactivate X-MuLV below the level of detection limit in a sample of mAb1 protein A eluate. (A) X-MuLV inactivation kinetics by low pH treatment and remaining viral infectivity during 240 minutes of incubation in a sample of mAb1 protein A eluate at 18° C. and pH 3.91, line in (—▣—) and (—▦—) are duplicate runs of the experiments. (B) X-MuLV inactivation kinetics by the dual treatment and remaining viral infectivity during 30 minutes of incubation in a sample of mAb1 protein A eluate at 16° C. and pH 3.91, the line in (—○—) shows the stability and the titers of a positive control, the line in (—◇—) shows X-MuLV inactivation kinetics and remaining viral infectivity during 30 minutes of incubation with 0.1% of Mega-10; the line in (—□—) shows X-MuLV inactivation kinetics and remaining viral infectivity during 30 minutes of incubation in a sample of mAb1 protein A eluate at pH 3.91; the line in (—△—) shows X-MuLV inactivation kinetics and remaining viral infectivity during 30 minutes of incubation in a sample of mAb1 protein A eluate at pH 3.91 and at the presence of 0.1% of Mega-10. (C) X-MuLV inactivation kinetics by low pH treatment and remaining viral infectivity during 240 minutes of incubation in a sample of mAb2 protein A eluate at 18° C. and pH 4.0. (D) X-MuLV inactivation kinetics by the dual treatment and remaining viral infectivity during 30 minutes of incubation in a sample of mAb2 protein A eluate at 16° C. and pH 4.05, the line in (—○—) shows the stability and the titers of a positive control, the line in (—⊖—) shows X-MuLV inactivation kinetics and remaining viral infectivity during 30 minutes of incubation with 0.15% of Mega-10; the line in (—□—) shows X-MuLV inactivation kinetics and remaining viral infectivity during 30 minutes of incubation in a sample of mAb2 protein A eluate at pH 4.05; the line in (—△—) shows X-MuLV inactivation kinetics and remaining viral infectivity during 30 minutes of incubation in a sample of mAb2 protein A eluate at pH 4.05 and at the presence of 0.15% of Mega-10.

Figure 5A:
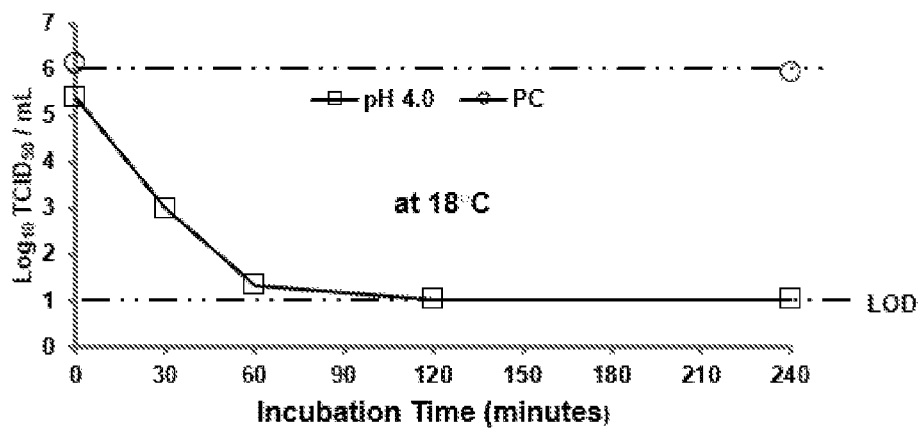

FIG. 5 shows the synergistic effects of dual treatment with low pH and Tween 80 on reducing time needed to inactivate X-MuLV below the level of detection limit in a sample of mAb2 protein A eluate. (A) X-MuLV inactivation kinetics by low pH treatment and remaining viral infectivity during 240 minutes of incubation in a sample of mAb2 protein A eluate at 18° C. and pH 4.0. (B) X-MuLV inactivation kinetics by the dual treatment and remaining viral infectivity during 30 minutes of incubation in a sample of mAb2 protein A eluate at 16° C. and pH 4.0, the line in (—○—) shows the stability and the titers of a positive control, the line in (—◇—) shows X-MuLV inactivation kinetics and remaining viral infectivity during 30 minutes of incubation with 0.5% of Tween 80; the line in (—□—) shows X-MuLV inactivation kinetics and remaining viral infectivity during 30 minutes of incubation in a sample of mAb2 protein A eluate at pH 4.0; the line in (—△—) shows X-MuLV inactivation kinetics and remaining viral infectivity during 30 minutes of incubation in a sample of mAb2 protein A eluate at pH 4.0 and at the presence of 0.5% of Tween 80.

Figure 6A:
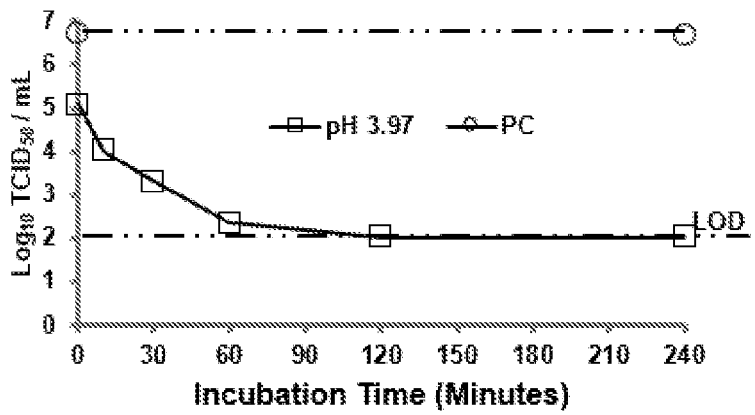

FIG. 6 shows the synergistic effects of dual treatment with low pH and Tween 80 or Tween 20 on reducing time needed to inactivate X-MuLV below the level of detection limit in a sample of mAb3 protein A eluate. (A) X-MuLV inactivation kinetics by low pH treatment and remaining viral infectivity during 240 minutes of incubation in a sample of mAb3 protein A eluate at 16° C. and pH 3.97. (B) X-MuLV inactivation kinetics by the dual treatment of low pH and Tween 80 and remaining viral infectivity during 60 minutes of incubation in a sample of mAb3 protein A eluate at 16° C. and pH 3.97, the line in (—○—) shows the stability and the titers of a positive control, the line in (—◇—) shows X-MuLV inactivation kinetics and remaining viral infectivity during 60 minutes of incubation with 0.5% of Tween 80; the line in (—□—) shows X-MuLV inactivation kinetics and remaining viral infectivity during 60 minutes of incubation in a sample of mAb3 protein A eluate at pH 3.97; the line in (—△—) shows X-MuLV inactivation kinetics and remaining viral infectivity during 60 minutes of incubation in a sample of mAb3 protein A eluate at pH 3.97 and at the presence of 0.5% of Tween 80. (C) X-MuLV inactivation kinetics by the dual treatment of low pH and 0.5% Tween 20 and remaining viral infectivity during 60 minutes of incubation in a sample of mAb3 protein A eluate at 16° C. and pH 3.97, the line in (—○—) shows the stability and the titers of a positive control, the line in (—⊖—) shows X-MuLV inactivation kinetics and remaining viral infectivity during 60 minutes of incubation with 0.5% of Tween 20; the line in (—□—) shows X-MuLV inactivation kinetics and remaining viral infectivity during 60 minutes of incubation in a sample of mAb3 protein A eluate at pH 3.97; the line in (—△—) shows X-MuLV inactivation kinetics and remaining viral infectivity during 60 minutes of incubation in a sample of mAb3 protein A eluate at pH 3.97 and at the presence of 0.5% of Tween 20.

FIG. 7 shows the effects of various concentration of Tween 80 and various pH value on dual treatment to reduce time required to inactivate X-MuLV below the level of detection limit in a sample of mAb3 protein A eluate. (A) X-MuLV inactivation kinetics by 0.1%, 0.2%, 0.3% and 0.5% of Tween 80 in a sample of mAb3 protein A eluate at 16° C. and pH 3.99. The line in (—○—) shows the stability and the titers of a positive control; the line in (—◇—) shows X-MuLV inactivation kinetics during 10 minutes of incubation in a sample of mAb3 protein A eluate at pH 3.99 containing 0.1% of Tween 80; the line in ( ) shows X-MuLV inactivation kinetics during 10 minutes of incubation in a sample of mAb3 protein A eluate at pH 3.99 containing 0.2% of Tween 80; the line in (—△—) shows X-MuLV inactivation kinetics during 10 minutes of incubation in a sample of mAb3 protein A eluate at pH 3.99 containing 0.3% of Tween 80; the line in (—□—) shows X-MuLV inactivation kinetics during 10 minutes of incubation in a sample of mAb3 protein A eluate at pH 3.99 containing 0.5% of Tween 80. (B) X-MuLV inactivation kinetics by 0.1% of Tween 80 in a sample of mAb3 protein A eluate at 16° C. and at pH 4.00, 3.90, 3.80 and 3.70. The line in ( ○ ) shows the stability and the titers of a positive control; the line in ( ◇ ) shows X-MuLV inactivation kinetics during 10 minutes of incubation in a sample of mAb3 protein A eluate at pH 4.00 containing 0.1% of Tween 80; the line in ( ▨ ) shows X-MuLV inactivation kinetics during 10 minutes of incubation in a sample of mAb3 protein A eluate at pH 3.90 containing 0.1% of Tween 80; the line in ( △ ) shows X-MuLV inactivation kinetics during 10 minutes of incubation in a sample of mAb3 protein A eluate at pH 3.80 containing 0.1% of Tween 80; the line in ( □ ) shows X-MuLV inactivation kinetics during 10 minutes of incubation in a sample of mAb3 protein A eluate at pH 3.70 containing 0.1% of Tween 80.

Figure 8A:
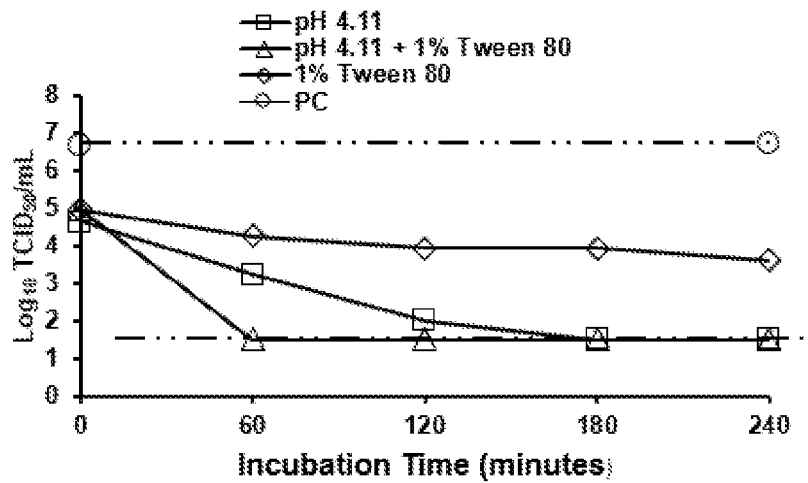
Figure 8B:
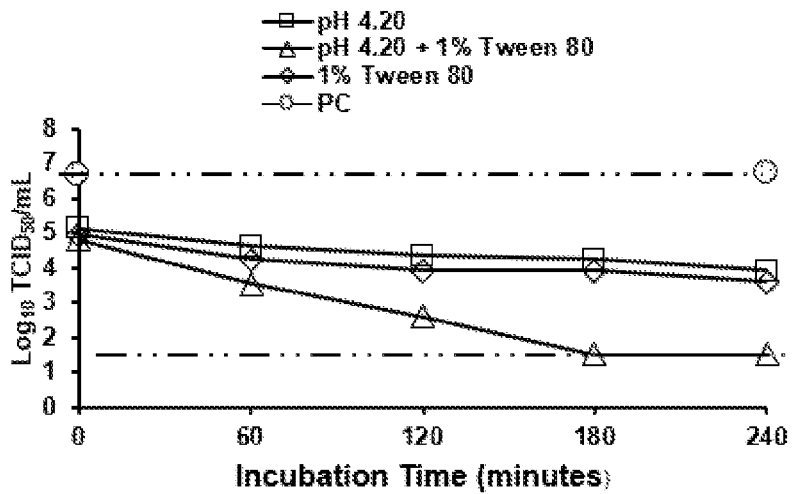
Figure 8C:
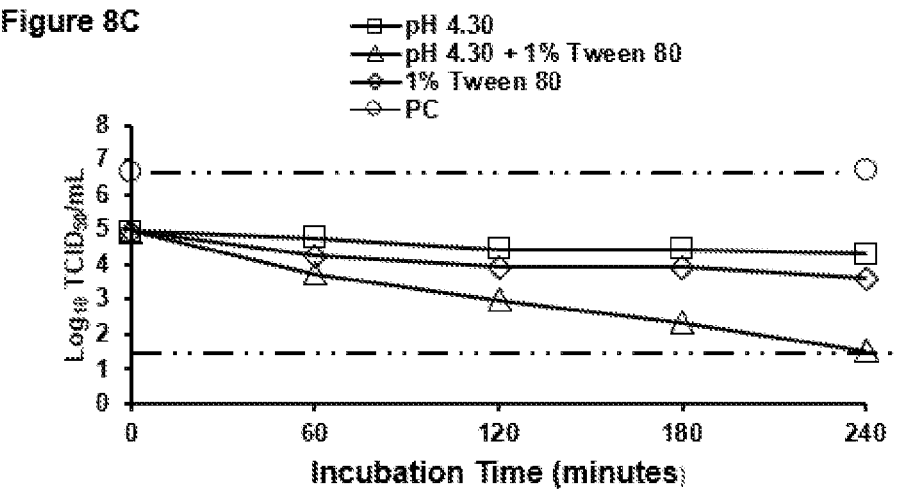

FIG. 8 shows simultaneous treatment of low pH and detergent could reduce time required for complete inactivation of X-MuLV by low pH even at pH value as high as 4.30. (A) X-MuLV inactivation kinetics by 1% of Tween 80 in a sample of mAb4 protein A eluate at 18° C. and pH 4.11. The line in ( ○ ) shows the stability and the titers of a positive control; the line in ( △ ) shows X-MuLV inactivation kinetics in a sample of mAb4 protein A eluate at pH 4.11 containing 1% of Tween 80; the line in ( □ ) shows X-MuLV inactivation kinetics in a sample of mAb4 protein A eluate at pH 4.11; the line in ( ◇ ) shows X-MuLV inactivation kinetics in a sample of mAb4 protein A eluate at pH 7.0 containing 1% of Tween 80; (B) X-MuLV inactivation kinetics by 1% of Tween 80 in a sample of mAb4 protein A eluate at 18° C. and pH 4.20. The line in ( ○ ) shows the stability and the titers of a positive control; the line in ( △ ) shows X-MuLV inactivation kinetics in a sample of mAb4 protein A eluate at pH 4.20 containing 1% of Tween 80; the line in ( □ ) shows X-MuLV inactivation kinetics in a sample of mAb4 protein A eluate at pH 4.20; the line in ( ◇ ) shows X-MuLV inactivation kinetics in a sample of mAb4 protein A eluate at pH 7.0 containing 1% of Tween 80; (C) X-MuLV inactivation kinetics by 1% of Tween 80 in a sample of mAb4 protein A eluate at 18° C. and pH 4.30. The line in ( ○ ) shows the stability and the titers of a positive control; the line in ( △ ) shows X-MuLV inactivation kinetics in a sample of mAb4 protein A eluate at pH 4.30 containing 1% of Tween 80; the line in ( □ ) shows X-MuLV inactivation kinetics in a sample of mAb4 protein A eluate at pH 4.30; the line in ( ◇ ) shows X-MuLV inactivation kinetics in a sample of mAb4 protein A eluate at pH 7.0 containing 1% of Tween 80.

DETAILED DESCRIPTION

This disclosure provides methods and compositions which relate to viral inactivation.

Definitions

For the purpose of interpreting this specification, the following definitions will apply. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

Whenever appropriate, terms used in the singular will also include the plural and vice versa. The use of "a" herein means "one or more" unless stated otherwise or where the use of "one or more" is clearly inappropriate. The use of "or" means "and/or" unless stated otherwise. The use of "comprise," "comprises," "comprising," "include," "includes," and "including" are interchangeable and are not limiting. The terms "such as," "for example," and "e.g." also are not intended to be limiting. For example, the term "including" shall mean "including, but not limited to."

As used herein, the term "about" refers to +/−10% of the unit value provided.

As used herein, the term "substantially" refers to the qualitative condition of exhibiting a total or approximate degree of a characteristic or property of interest. One of ordinary skill in the biological arts will understand that biological and chemical phenomena rarely, if ever, achieve or avoid an absolute result because of the many variables that affect testing, production, and storage of biological and chemical compositions and materials, and because of the inherent error in the instruments and equipment used in the testing, production, and storage of biological and chemical compositions and materials. The term "substantially" is, therefore, used herein to capture the potential lack of completeness inherent in many biological and chemical phenomena.

As used herein, the term "orthogonal" refers to separate identifiable steps or processes that employ a distinct mechanism to remove/inactivate viruses. As it relates to process development, this is generally understood to mean that multistep purification procedures should employ separation mechanisms that are distinct from one another; each step representing an axis in Cartesian space. A two-step process employing anion exchange and hydrophobic interaction chromatography (HIC) would be understood to be orthogonal.

Since the 1980s, detergents have been used as an essential tool to inactivate viruses in pooled blood collected from blood donors. This process is important for the safety of the patients receiving blood, plasma or blood/plasma derived components, such as plasma derived Factor VIII (pdFVIII). Additionally, this purification measure increases the safety for personnel directly involved in the processing of blood in clinical laboratories or in manufacturing facilities of plasma derived biological products (PDBP). More recently, this practice has also become integral to the biopharmaceutical drug manufacturing process for biological therapeutics or vaccines using animal-derived materials. Animal-derived materials (i.e. blood, plasma, tissues), and proteins produced in mammalian cells may carry endogenous viruses or may easily become contaminated with adventitious viruses. Therefore, the drug manufacturing process comprises a series of effective virus inactivation (i.e. solvent-detergent, low pH, and heat treatments) and removal technologies (i.e. viral filtration) to ensure patients receive virus free biotherapeutic products. These processes are vital to the safety of the biologically-derived therapeutic or vaccine products. Novel methods to increase the efficiency, robustness, and most importantly, and the overall safety of these products are in great need.

Types of Detergents

Detergents are amphiphilic molecules that consist of a hydrophilic (polar) head group and a hydrophobic (nonpolar) tail group. This universal structure allows for the interaction of detergents with other molecules, most notably, proteins or enveloped viruses in an aqueous solution. In basic science and applied technologies, detergents can be used as a solubilizing agent or as a stabilizing agent to prevent biological molecules from aggregation or to solubilize membrane proteins from cell cultures or tissue suspensions. When used for solubilizing proteins, the following properties make certain detergents more desirable than others: 1) Detergents that lack charges (nonionic detergents) help retain the structure and activity of the protein of interest; 2) detergents with a low critical micelle concentration (CMC) allow for easy removal of the detergent via dialysis; 3) detergents that are clear and, therefore, do not affect protein absorbency readings; and 4) detergents that are highly pure, decreasing variability from experiment to experiment. Similarly, most of these properties are applicable when choosing detergent candidates for virus inactivation as it is necessary to not disrupt the protein drug, to detect protein concentration without interference from the detergent, and to ensure that the detergent is highly pure so viral inactivation consistently occurs.

Generally, enveloped virus inactivation is dependent on the amphiphilic structure and the critical micelle concentration (CMC) of the specific detergent. The CMC refers to the concentration at which detergent monomers aggregate to form micelle structures. In aqueous solutions, as more detergent monomers come in contact, the hydrophilic heads can adjoin to shield the hydrophobic tails from the aqueous solution, ultimately organizing into micelle structures. CMC is likely linked to the concentration at which viral inactivation will occur for a given detergent under specific conditions. A theoretical mechanism for virus inactivation is that the monomers insert into the viral envelope below the detergent CMC, which may be detrimental to the virus. As soon as the concentration is at or above the CMC, the detergent monomers present in the membrane form micelles that can disrupt the integrity or completely strip the viral envelope. Without the viral envelope, the virus is unable to bind to its receptor on the plasma membrane of its host cells and facilitate its replication and spread.

Thus far, the bio-therapeutic manufacturing industry has used a few detergents for inactivating enveloped viruses. One of the popular nonionic detergents, Triton X-100, has been effective at inactivating enveloped viruses without disrupting the protein drug. After the use of Triton X-100 in the biopharmaceutical manufacturing processes, it is disposed into the waste water treatment plants or is directly released into the aquatic environment (Madsen et al, 1996, JAOCS, 73:929-933). Unfortunately, the Triton X-100 by-product contains octylphenol which has been deemed a toxic chemical to the environment by a number of countries. Many biopharmaceutical industries have, therefore, been dedicated to search for environmentally safer detergents that have comparable efficacy to Triton X-100. For example, some companies have been researching Lauryl dimethylamine N-oxide (LDAO) and alkyl glucosides, respectively (Conley et al., 2014, US Patent #W02014025771A2; Conley et al., 2016, Biotechnol. Bioeng., Epub ahead of print; Fisher et al., 2016, US Patent #20160333046A1). While these companies have been able to distinguish new detergents of different classes, the present embodiments define a completely novel and highly effective class of nonionic detergents used in the inactivation of enveloped viruses.

Sugar-based detergents have excellent physical properties, are highly biodegradable and non-toxic, which contribute to its safety profile, especially for the aquatic environment (Bogdan, 2007, Stalmans et al., 1993). Thus, the disclosed embodiments are focused on the use of the sugar-based detergents, N-methylglucamides, as a new method to inactivate viruses in bioactive-drug manufacturing. N-methylglucamides are nonionic detergents that are composed of a highly hydrophilic glucose moiety and hydrophobic fatty acid chain linked by an amide bond. These detergents are ecofriendly as they are known to be highly biodegradable with about a 95% renewable carbon index and are considered non-toxic especially to aquatic life (Stalmans et al., 1993, SOFW, 119:794-808).

Mega-10 is a sugar-based nonionic detergent that is composed of a highly hydrophilic glucose moiety and hydrophobic fatty acid chain linked by an amide bond, which makes it highly biodegradable with about a 95% renewable carbon index and without toxicity to the aquatic environment (Burczyk, B., Wilk, K. A., Sokolowski, A., and Syper, L., 2001) (Foley, P., Pour, A. K., Beach, E. S., and Zimmerman, J. B., 2012). Furthermore, it was observed for the first time that a dual treatment of low pH in the presence of a detergent such as Mega-10 or Tween 80 or Tween 20 could have a synergistic effect on reducing viral infectivity and the time needed to effectively inactivate retroviruses. These dual mechanisms of viral inactivation could have a potential utility in viral inactivation of monoclonal antibodies manufactured by continuous processing.

Viruses, Proteins and Detergents

The model enveloped virus used for evaluation of viral inactivation was Xenotropic Murine Leukemia Virus (X-MuLV) that was purchased from BioReliance (Rockvile, Md.). X-MuLV was chosen as a specific model virus for the low pH and detergent inactivation studies because it resembles the endogenous retrovirus-like particles (ERLPs) commonly found in mammalian culture production.

Model proteins, a sample of mAb1 ($IgG_1$), a sample of mAb2 ($IgG_1$), and a sample of mAb3 ($IgG_2$) were collected as eluate pools of protein A affinity column chromatography following the clarification of their respective cell culture. The isoelectric point (pI) values of these mAbs were 8.9, 7.1 and 7.7, respectively.

N-Methylglucamide (Mega-10), Tween 20 and Tween 80 were purchased from Sigma-Aldrich (St. Louis, Mo.). A 5% of Mega-10 stock solution (w/v) was prepared by dissolving 0.5 gram of Mega-10 powder in 10 mL of Milli-Q water. A stock solution of Tween 20 or Tween 80 detergent was prepared at 5% concentration (w/v) by Milli-Q water.

Viral Inactivation Experiments

Viral Inactivation by Detergents

The pH of various protein A eluates was adjusted to 7.0 with 1M Tris buffer. The pH adjusted eluate was then filtered through a 0.22 um filter. Various volumes of 5% stock solution of Mega-10, Tween 20, or Tween 80 were added to the filtered neutralized protein A eluates. This was done to prepare protein A eluates containing various concentrations of each detergent. X-MuLV was then spiked at a 1:20 ratio to the neutralized protein A eluate containing various concentrations of each detergent that had been pre-incubated at a 16° C. water bath prior to the virus spiking. After a thorough mixing, an aliquot of a sample was removed immediately and quenched with a diluent (McCoy's medium containing 3 μg/mL of polybrene) at 1:12 for Mega-10 or at 1:100 for Tween 20 and Tween 80 to stop the inactivation, and the sample was designated as a time-zero sample. The remaining spiked eluate was returned to the water bath and the samples were collected at the indicated time to evaluate the viral inactivation kinetics.

Viral Inactivation by Low pH

The pH of mAb1, mAb2, and mAb3 protein A eluates was adjusted to 3.91, 4.05 or 3.97 with 1M acetic acid. The pH-adjusted eluates were then filtered by a 0.22 um filter. The filtered protein A eluates were pre-incubated at a 16° C. water bath prior to spiking with X-MuLV at a 1:20 ratio. After a thorough mixing, an aliquot of sample was removed immediately and neutralized with 1 M Tris buffer to quench inactivation and was designated as a time-zero sample. The remaining spiked eluates were returned to the water bath and the samples were collected at indicated times to evaluate the viral inactivation kinetics.

Dual Viral Inactivation by Low pH and Detergent

The pH of mAb1, mAb2, and mAb3 protein A eluates was adjusted to 3.91, 4.05 or 3.97 with 1M acetic acid. The pH adjusted eluates were then filtered by a 0.22 um filter. Various volumes of 5% detergent stock solution were then added to the filtered protein A eluates. The low pH protein A eluates containing Mega-10, Tween 80 or Tween 20 were pre-incubated at a 16° C. water bath prior to spiking with X-MuLV at a 1:20 ratio. After a thorough mixing, an aliquot of sample was removed immediately and neutralized with 1 M Tris buffer to stop low pH viral inactivation, then immediately quenched with diluent at 1:12 for Mega-10 or at 1:100 for Tween 20 and Tween 80 to stop viral inactivation by the detergent. The collected sample was designated as a time-zero reference. The remaining spiked eluate was returned to the water bath and the samples were collected at indicated times to evaluate the viral inactivation kinetics.

X-MuLV Cell-Based Infectivity Assay

The remaining X-MuLV infectivity in the samples post-inactivation treatment was determined by a $TCID_{50}$ assay that is an endpoint dilution assay to quantify the amount of virus required to produce a cytopathic effect in 50% of inoculated tissue culture cells. Virus titers were estimated using the Spearman-Karber method and reported as $TCID_{50}$/mL with a calculated 95% confidence interval (CI). Briefly, a sufficient number of 96-well plates with PG-4 (feline $S^+L^-$, ATCC#CRL-2032) cells were prepared the day before starting the viral inactivation experiments and incubated overnight in a 37° C. humidified $CO_2$ incubator. A set of ten 3.2 fold dilution of the diluted positive control (1:100) and viral inactivated samples were prepared in a dilution block. Each set of the 11 serial dilutions of the samples were inoculated correspondingly onto wells (100 μL per well) of the first 11 columns in a 96-well plate that had been pre-seeded with PG-4 cells. The $12^{th}$ column in the same plate was inoculated with the corresponding diluent to serve as non-virus negative control. The positive control was prepared by spiking the filtered neutralized protein A eluate with X-MuLV at a 1:20 ratio. The inoculated plates were then incubated in a 37° C. humidified $CO_2$ incubator for approximate 2 hours. A volume of 100 uL of 2× assay medium (92% McCoy's 5A medium, 4% FBS, 2% Penicillin/Streptomycin, 2% L-Glutamine) was added to each well of the plates at the end of incubation. The plates were then returned to the same incubator, and continued incubation for 6 days. Each well of the plates were scored under a microscope for the presence of cytopathic effect (CPE) and the results were recorded in a scoring sheet. Virus titers were then estimated using the Spearman-Karber method and reported as $TCID_{50}$/mL with a calculated 95% confidence interval (CI).

Robustness of X-MuLV Inactivation by Mega-10 in Protein a Eluates of mAb

Figure 1A:
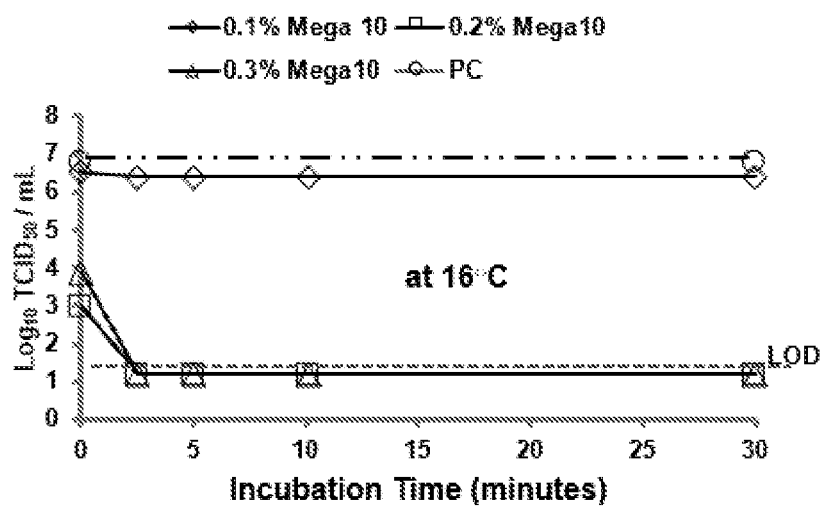
FIG. 1 shows the Kinetics of X-MuLV inactivation by various concentration of Mega-10 at 16° C. in a sample of (A) mAb1 protein A eluate at pH 7.01 and (B) a sample of mAb2 protein A eluate at pH 7.01. X-MuLV was spiked into the neutralized antibody protein A eluate containing various concentration of Mega-10. After thoroughly mixing, the mixture was incubated in a water bath set at 16° C. and an aliquot of a sample was removed at the indicated time to evaluate the viral inactivation kinetics by a $TCID_{50}$ assay.

To evaluate robustness of X-MuLV inactivation by Mega-10 in Protein A eluates of mAb1, X-MuLV was spiked at a 1:20 ratio into the neutralized mAb1 protein A eluate contain 0.1%, 0.2% and 0.3% of Mega-10. After a thorough mixing, an aliquot of sample was removed at 0, 2.5, 5, 10, and 30 minutes after incubation at 16° C. The remaining virus titer in the collected samples was determined by the $TCID_{50}$ assay. Results of the $TCID_{50}$ assay showed that Mega-10 at 0.2% and 0.3% concentration inactivated X-MuLV rapidly to the level below the detection limit after a treatment of 2.5 minutes (FIG. 1A) and achieved LRF values of ≥5.58±0.19 and ≥5.58±0.19, respectively (Table 1A).

TABLE 1A

Effects of X-MuLV Inactivation by Mega-10 in mAb1 Protein A Eluate

| | 0.1% Mega-10 | | 0.2% Mega-10 | | 0.3% Mega-10 | |
|---|---|---|---|---|---|---|
| Incubation Time (Minutes) | $Log_{10}$ $TCID_{50}$/mL | LRF ± 95% CL | $Log_{10}$ $TCID_{50}$/mL | LRF ± 95% CL | $Log_{10}$ $TCID_{50}$/mL | LRF ± 95% CL |
| 0 | 6.53 ± 0.20 | 0.26 ± 0.28 | 3.88 ± 0.25 | 2.91 ± 0.32 | 3.00 ± 0.27 | 3.79 ± 0.33 |
| 2.5 | 6.41 ± 0.26 | 0.38 ± 0.32 | ≤1.21 ± n/a | ≥5.58 ± 0.19 | ≤1.21 ± n/a | ≥5.58 ± 0.19 |
| 5.0 | 6.41 ± 0.21 | 0.38 ± 0.28 | ≤1.21 ± n/a | ≥5.58 ± 0.19 | ≤1.21 ± n/a | ≥5.58 ± 0.19 |
| 10 | 6.41 ± 0.20 | 0.38 ± 0.28 | ≤1.21 ± n/a | ≥5.58 ± 0.19 | ≤1.21 ± n/a | ≥5.58 ± 0.19 |
| 30 | 6.41 ± 0.12 | 0.38 ± 0.23 | ≤1.21 ± n/a | ≥5.58 ± 0.19 | ≤1.21 ± n/a | ≥5.58 ± 0.19 |

Figure 1B:
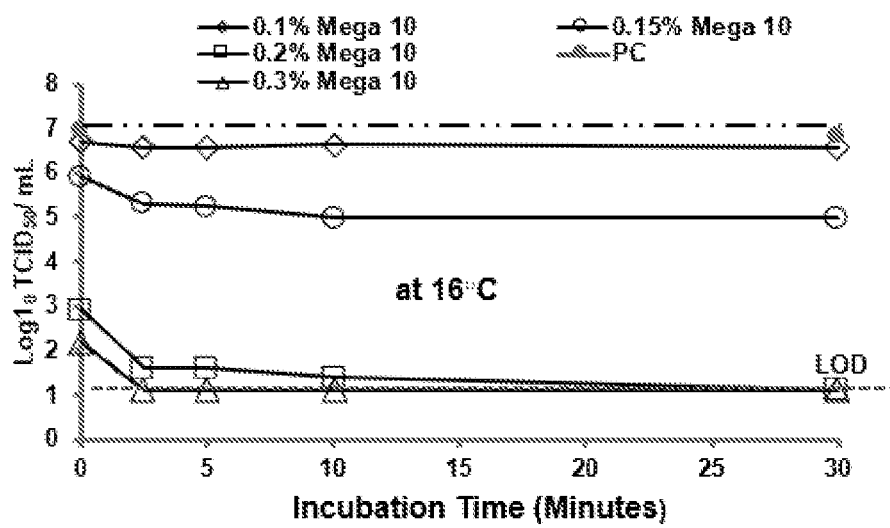

The effectiveness of the Mega-10 detergent to inactivate viruses was also evaluated on the Protein A eluates of the second mAb product, mAb2 sample. Similar effects of viral inactivation were observed when X-MuLV was incubated with the neutralized mAb2 protein A eluate containing 0.1%, 0.15%, 0.2% and 0.3% of Mega-10 (FIG. 1B). Mega-10 at 0.3% concentration was shown to inactivate X-MuLV rapidly to the level below detection after a treatment of 2.5 minutes and achieved a value of LRF of ≥5.81±0.18 (Table 1B). Significant viral inactivation was also achieved by 0.2% Mega-10 after 2.5 minutes treatment with a LRF of 5.31±0.75 (Table 1B).

TABLE 1B

Effects of X-MuLV Inactivation by Mega-10 in mAb2 Protein A Eluate

| | 0.1% Mega-10 | | 0.2% Mega-10 | | 0.3% Mega-10 | |
|---|---|---|---|---|---|---|
| Incubation Time (Minutes) | $Log_{10}$ $TCID_{50}$/mL | LRF ± 95% CL | $Log_{10}$ $TCID_{50}$/mL | LRF ± 95% CL | $Log_{10}$ $TCID_{50}$/mL | LRF ± 95% CL |
| 0 | 6.56 ± 0.22 | 0.36 ± 0.28 | 2.19 ± 0.43 | 4.73 ± 0.46 | 2.19 ± 0.43 | 4.73 ± 0.46 |
| 2.5 | 6.56 ± 0.22 | 0.36 ± 0.28 | 1.61 ± 0.73 | 5.31 ± 0.75 | ≤1.11 ± n/a | ≥5.81 ± 0.18 |
| 5.0 | 6.56 ± 0.18 | 0.36 ± 0.25 | 1.61 ± 0.73 | 5.31 ± 0.75 | ≤1.11 ± n/a | ≥5.81 ± 0.18 |

TABLE 1B-continued

Effects of X-MuLV Inactivation by Mega-10 in mAb2 Protein A Eluate

| | 0.1% Mega-10 | | 0.2% Mega-10 | | 0.3% Mega-10 | |
|---|---|---|---|---|---|---|
| Incubation Time (Minutes) | $Log_{10}$ $TCID_{50}$/mL | LRF ± 95% CL | $Log_{10}$ $TCID_{50}$/mL | LRF ± 95% CL | $Log_{10}$ $TCID_{50}$/mL | LRF ± 95% CL |
| 10 | 6.63 ± 0.19 | 0.29 ± 0.26 | 1.42 ± 0.88 | 5.50 ± 0.90 | ≤1.11 ± n/a | ≥5.81 ± 0.18 |
| 30 | 6.56 ± 0.22 | 0.36 ± 0.28 | ≤1.11 ± 0.27 | ≥5.81 ± 0.32 | ≤1.11 ± n/a | ≥5.81 ± 0.18 |

Synergistic Effects of Low pH and Mega-10 Dual Treatment on Reducing Infectivity of X-MuLV The mechanism employed by detergents to inactivate enveloped viruses has been attributed to the interaction of detergent with the lipid membrane of enveloped virus. The interaction disrupts membranes and causes the disintegration of the viral capsid proteins, which in turn prevents the binding of enveloped virus to the cells, leading to a loss of virus infectivity (Pamphilon, 2000) (Kempf, C., Stucki, M., and Boschetti, N., 2007). Low pH-mediated virus inactivation, on the other hand, is believed to act through another mechanism. A low pH environment induces virus morphology changes leading to virus particle aggregation which has been implicated as the mechanism for low pH viral inactivation (Gaudin, Y., Ruigrok, R., Knossow, M., and Flamand, A., 1993).

As the underlying mechanisms for detergent and low pH to inactivate enveloped viruses are very different, it would not be intuitive or obvious to combine these treatments together.

Figure 2:
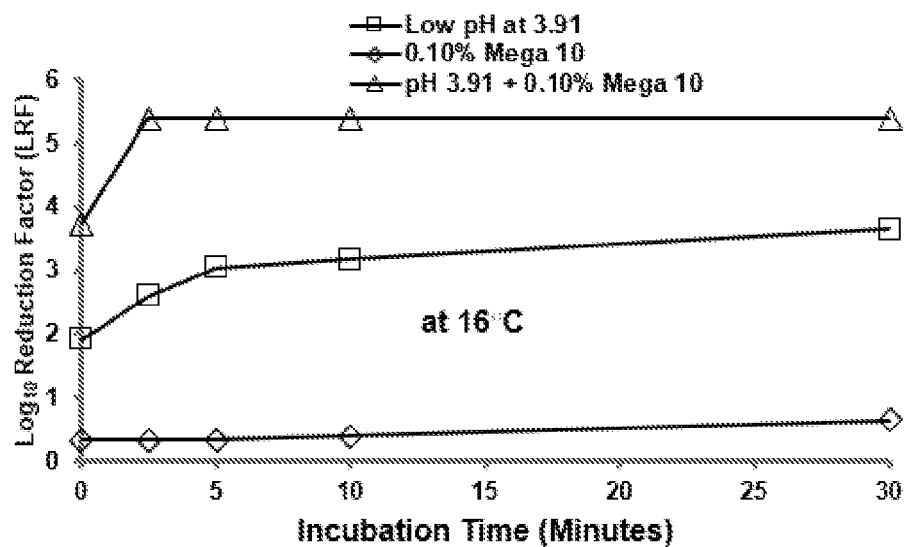
FIG. 2 shows the synergistic effects of dual treatment with low pH and Mega-10 on reducing X-MuLV infectivity after incubation at 16° C. in a sample of mAb1 protein A eluate. The line in ( –◇– ) shows X-MuLV inactivation kinetics and Log 10 Reduction Factor (LRF) achieved during 30 minutes of incubation with 0.10% of Mega-10; the line ( –◻– )

The inactivation of X-MuLV was carried out under the conditions that were sub-optimal for both low pH and detergent-mediated viral inactivation. Miraculously, a synergistic effect on reducing the infectivity of X-MuLV was observed when X-MuLV was incubated with the sample of mAb1 protein A eluate containing 0.1% of Mega-10 at pH 3.91 (FIG. 2 and Table 2). After an incubation of 2.5 minutes, samples of 0.1% of Mega-10 showed no effects on X-MuLV inactivation and generated a LRF of 0.33±0.29. A treatment by pH 3.91 alone generated modest reduction of viral infectivity with a LRF of 2.60±0.33 after the same incubation time. Surprisingly, the dual treatment of 0.1% Mega-10 and pH 3.91 effectively inactivated X-MuLV to the level below the detection limit and generated a LRF of ≥5.40±0.21 after the same incubation time. Similar effects were also observed when X-MuLV inactivation was carried out on a mAb2 protein A eluate sample containing 0.15% of Mega-10 at pH 4.05 (FIG. 3 and Table 3).

TABLE 2

LRF Achieved by Various Treatments in mAb1 Protein A Eluate

| Time (minutes) | Low pH at 3.91 LRF ± 95% CL | 0.10% Mega 10 LRF ± 95% CL | pH 3.91 + 0.10% Mega 10 LRF ± 95% CL |
|---|---|---|---|
| 0 | 1.91 ± 0.36 | 0.33 ± 0.35 | 3.74 ± 0.33 |
| 2.5 | 2.60 ± 0.33 | 0.33 ± 0.29 | ≥5.40 ± 0.21 |
| 5 | 3.04 ± 0.32 | 0.33 ± 0.32 | ≥5.40 ± 0.21 |
| 10 | 3.17 ± 0.27 | 0.39 ± 0.36 | ≥5.40 ± 0.21 |
| 30 | 3.64 ± 0.37 | 0.64 ± 0.33 | ≥5.40 ± 0.21 |

TABLE 3

LRF Achieved by Various Treatments in mAb2 Protein A Eluate

| Time (minutes) | Low pH at 4.05 LRF ± 95% CL | 0.15% Mega 10 LRF ± 95% CL | pH 4.05 + 0.15% Mega 10 LRF ± 95% CL |
|---|---|---|---|
| 0 | 0.17 ± 0.18 | 0.99 ± 0.30 | 1.62 ± 0.27 |
| 2.5 | 0.55 ± 0.18 | 1.62 ± 0.30 | 3.96 ± 0.31 |
| 5 | 0.61 ± 0.18 | 1.68 ± 0.31 | 5.50 ± 0.83 |
| 10 | 0.67 ± 0.18 | 1.94 ± 0.32 | ≥5.81 ± 0.18 |
| 30 | 0.55 ± 0.18 | 1.94 ± 0.32 | ≥5.81 ± 0.18 |

After 5 minutes of incubation, 0.15% of Mega-10 only generated a LRF of 1.68±0.31 and a treatment by pH 4.05 alone generated a LRF of 0.61±0.18. However, dual treatment of 0.15% of Mega-10 and pH 4.05 generated a LRF of 5.50±0.83, which was far greater than the sum of their individual effects. Therefore, it can be surmised that treatment of Protein A eluate at a low pH in the presence of a detergent has a synergistic effect on reducing infectivity of enveloped viruses due to the dual orthogonal mechanisms of viral inactivation.

Figure 4A:
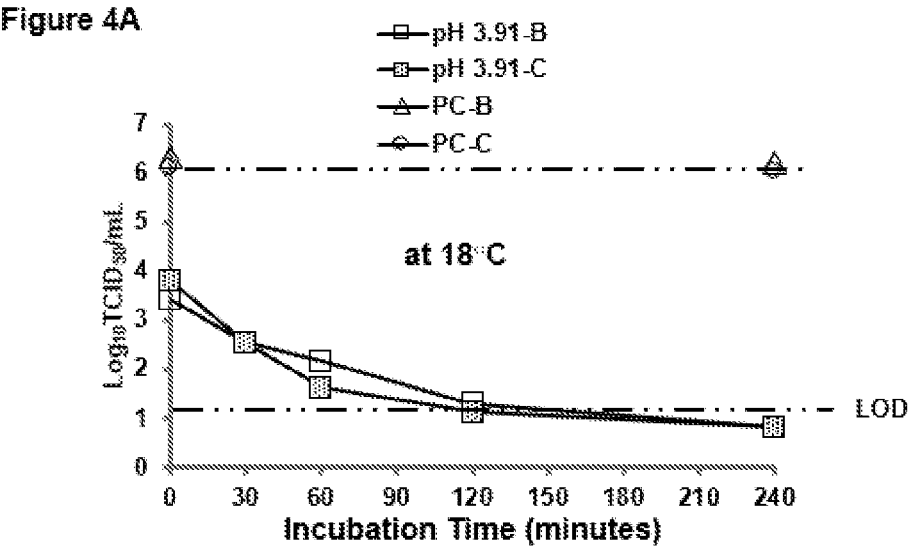
Figure 4B:
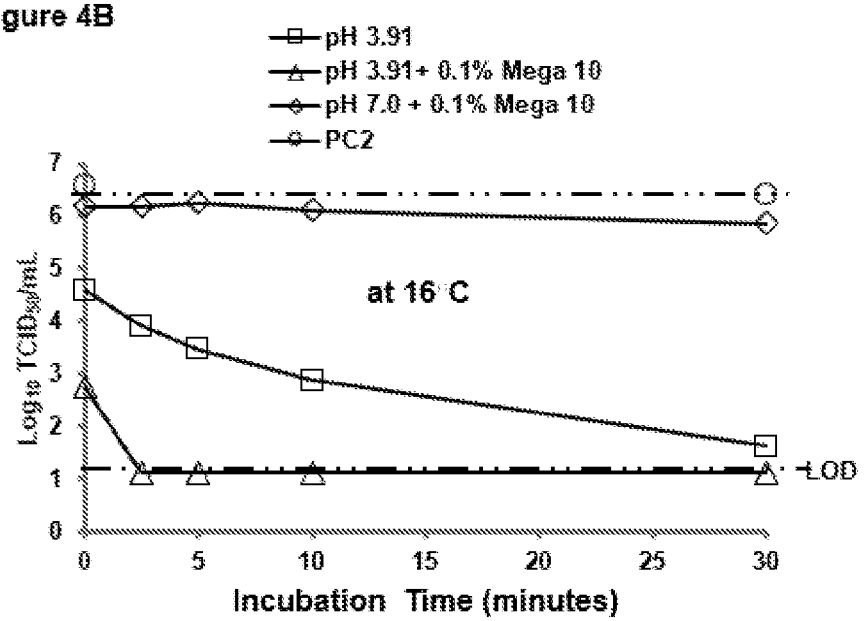
Figure 4C:
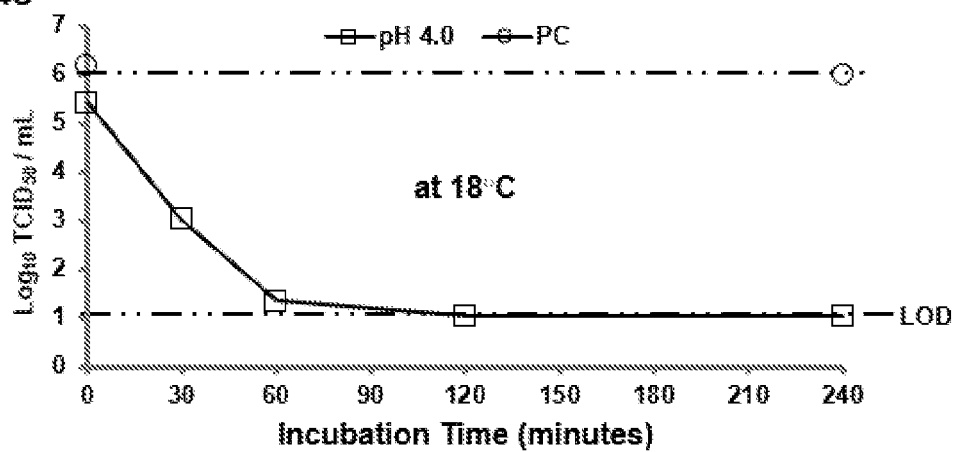
Figure 4D:
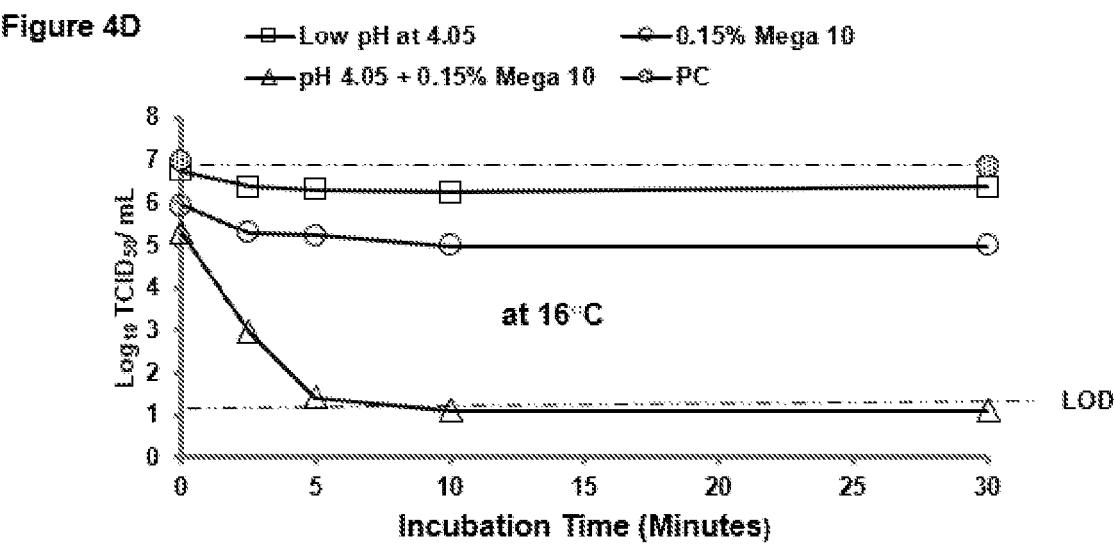

Synergistic Effects of Low pH and Detergent Dual Treatment on Reducing the Time Needed to Inactivate X-MuLV to the Level Below Detection In addition to the synergistic effects of low pH and Mega-10 dual treatment on reducing infectivity of X-MuLV, we also observed the synergistic effects of a simultaneous low pH and Mega-10 treatment on reducing the duration of treatment needed to inactivate X-MuLV to the level below the detection limit or completely inactivate X-MuLV. As shown in FIG. 4A, it took 240 minutes to inactivate X-MuLV to the level below the detection limit when a sample of mAb1 protein A eluate was incubated at pH 3.91 and 18° C. (FIG. 4A). Strikingly, it only took 2.5 minutes to inactivate X-MuLV to the level below the detection limit after incubating the same protein A eluate at pH 3.91 with the presence of additional 0.1% of Mega-10 at a temperature of 16° C. (FIG. 4B). Similarly, dual treatment of X-MuLV in a sample of the different mAb, mAb2 protein A eluate containing 0.15% of Mega-10 at pH 4.05 and a temperature of 16° C. was also able to reduce the time needed for inactivating X-MuLV to the level below the detection limit from 120 minutes of incubation at a lower pH (pH 4.0) and a higher temperature (18° C.) (FIG. 4C) to just 10 minutes (FIG. 4D).

Figure 5B:
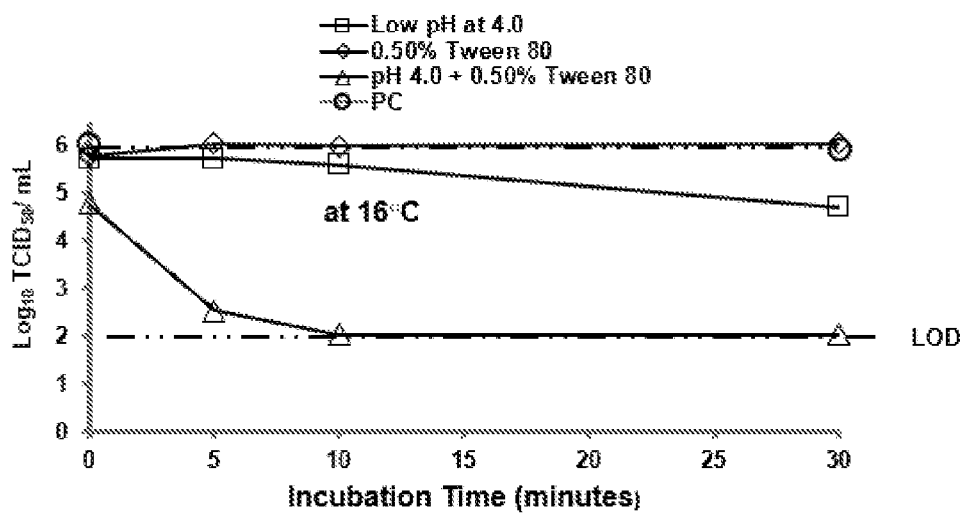
Figure 6B:
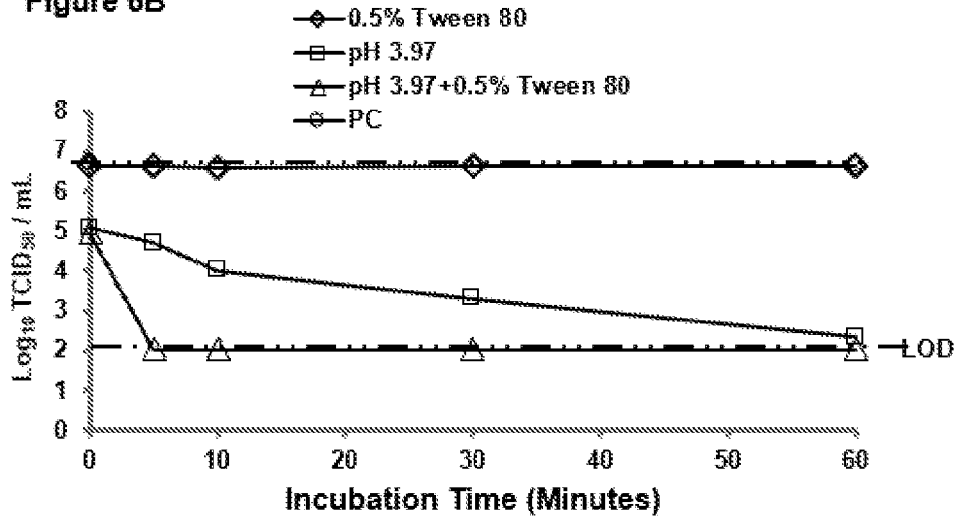
Figure 6C:
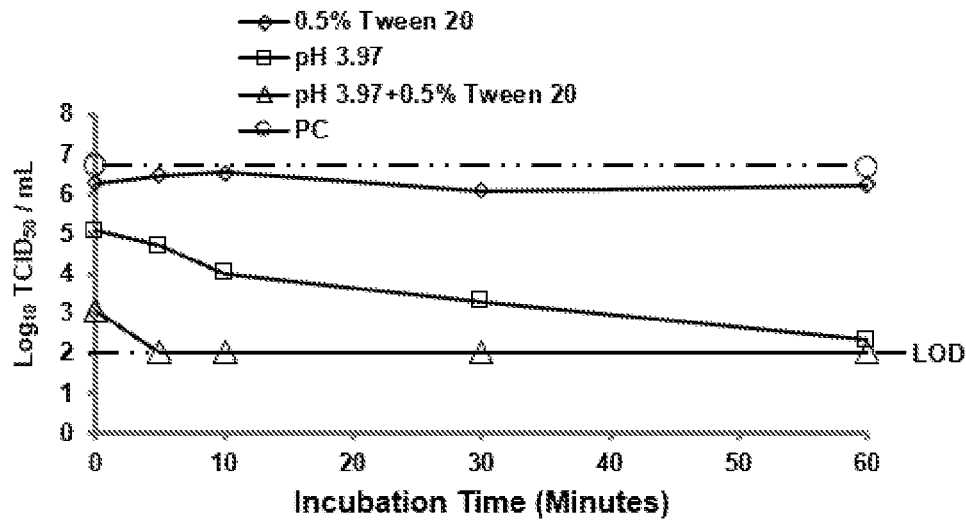

We further investigated whether the observed synergistic effects of dual treatment on viral inactivation was limited to only the Mega-10 detergent. Experiments were carried out for X-MuLV inactivation at low pH in the presence of other non-ionic detergents such as Tween 80 or Tween 20. A dual treatment of X-MuLV on mAb2protein A eluates containing 0.5% of Tween 80 at pH 4.05 and a temperature of 16° C. were also able to reduce the time needed for inactivating X-MuLV to the level below the detection limit from 120 minutes of incubation at pH 4.0 and a higher temperature (18° C.) (FIG. 5A) to 10 minutes (FIG. 5B). Similar synergistic effects were also observed when dual viral inactivation was carried out on a different subtype of mAb3 (IgG2) protein A eluate containing 0.5% of Tween 80 (FIG. 6B) or 0.5% Tween 20 (FIG. 6C) at pH 3.97. In either case, the incubation time needed for inactivation of X-MuLV to the level below the detection limit was reduced from 120 minutes by low pH treatment alone (FIG. 6A) to 5 minutes (FIGS. 6B and 6C).

Figure 7A:
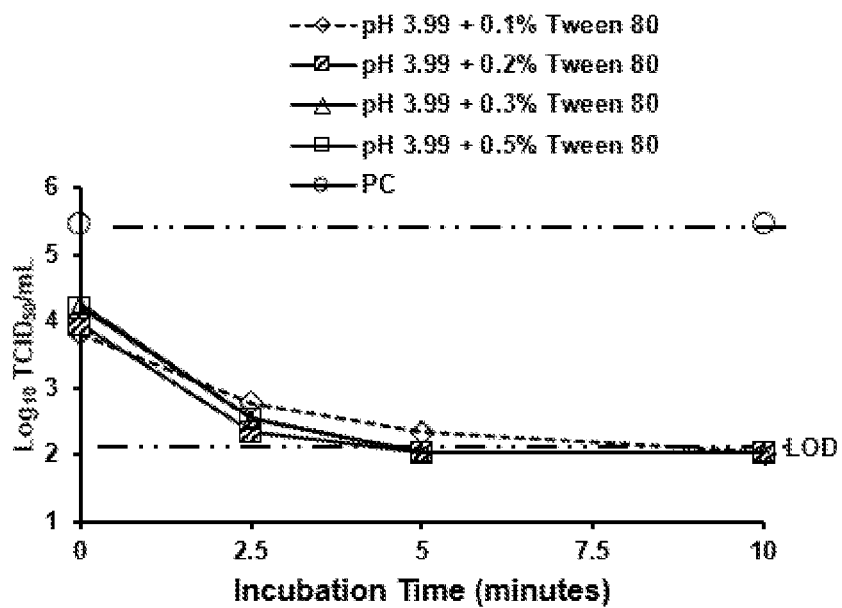
Figure 7B:
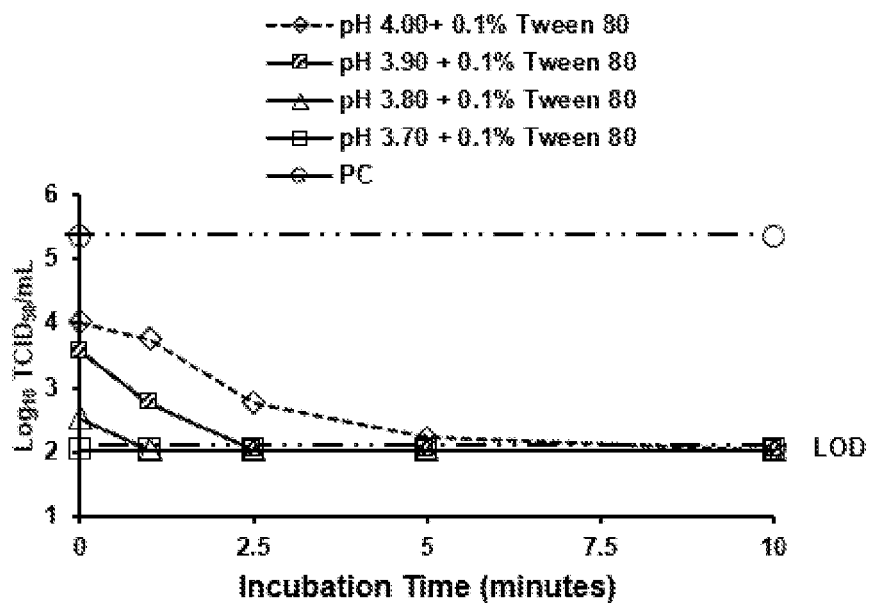

We further demonstrated that addition of minimum concentration of 0.2% of Tween 80 to Protein A eluate at pH 3.99 is enough to reduce required inactivation time from 120 minutes to 5 minutes and no further reducing of time was observed while the concentration of Tween 80 was increased to 0.3% or 0.5% (FIG. 7A). On the other hand, the time required for X-MuLV inactivation was reduced from 10 minutes to 2.5 minutes, 1 minute, then 0 minute respectively as the pH value of mAb3 protein A eluate containing 0.1% Tween 80 decreases from 4.0 to 3.9, 3.8 then 3.7 (FIG. 7B). Hereby, the time required for X-MuLV inactivation by simultaneous dual treatment decreases as the concentration of detergent increases and the pH value of protein A eluate decreases. In addition, the minimum effective concentration of Tween 80 needed for the dual treatment is pH dependent, the lower minimum effective concentration is needed for the lower pH value.

We also demonstrated simultaneous treatment of low pH and detergent could reduce time required for complete inactivation of X-MuLV by low pH even at pH value as high as 4.30. Protein A eluate of mAb4 at pH 4.11, 4.20 or 4.30 containing 1% Tween 80 was able to completely inactivate X-MuLV respectively after 1, 3 or 4 hours of treatment, which makes it possible to carry out the low pH viral inactivation step of antibody manufacturing without any pH adjustment for the pH value of protein A eluate below 4.30 with 1% Tween 80 or as high as pH 4.50 with Tween 20 or Triton X-100. Currently, low pH viral inactivation is carried out at pH 3.70 to 3.90 through adjusting pH of protein A eluate commonly with value of pH from 4.10 to 4.50. Thus, carrying out low pH viral inactivation without adjusting pH of protein A eluate could fast make the antibody purification process faster and more efficient (FIG. 8).

As discussed, the present embodiments demonstrate that the eco-friendly detergent, Mega-10, can effectively inactivate a model enveloped virus, X-MuLV, at a low concentration on the neutralized protein A eluate of monoclonal antibodies. Thus, detergent viral inactivation for enveloped viruses by Mega-10 could be incorporated into a monoclonal antibody manufacturing process as a robust viral inactivation step following low pH viral inactivation. To achieve a LRF of ≥4.0 retroviral inactivation on a clarified, cell-free intermediate of mAb or IgG Fc fusion protein at pH 6.0-8.0, a concentration of Triton X-100≥0.5% and a hold time ≥60 minutes at a temperature of 15-25° C. is needed, but with Mega-10, a LRF of ≥5.81 viral inactivation on the neutralized protein A eluate (pH 7.0) of monoclonal antibodies can be achieved at a concentration of 0.2% after a hold time of 30 minutes at 16° C. Hence, Mega-10 could be a viable alternative to Triton X-100 for use as a viral inactivation detergent in monoclonal antibody manufacturing as Mega-10 is more effective than Triton X-100 on inactivation of retroviruses and is highly biodegradable with no toxicity to the aquatic environment.

We also observed for the first time that a simultaneous dual treatment of low pH and a detergent such as Mega-10, or Tween 80, or Tween 20 could have a synergistic effect on reducing viral infectivity and the time needed to effectively inactivate retroviruses. For instance, a 2.5 minute treatment of X-MuLV by 0.1% of Mega-10 present on the neutralized protein A eluate of a sample or by pH 3.91 of protein A eluate generated a LRF of 0.33±0.29 and 2.50±0.33, respectively. A dual treatment of X-MuLV by 0.1% Mega-10 in the presence pH 3.91 protein A eluate (simultaneous low pH and detergent treatment) for 2.5 minutes effectively inactivated X-MuLV to a level below the detection limit and generated a LRF of ≥5.40±0.21. Similar effects were also observed when X-MuLV inactivation was carried out in the sample protein A eluate at pH 4.05 containing 0.15% of Mega-10. While a 5 minute treatment of X-MuLV by 0.15% of Mega-10 present on the neutralized protein A eluate or by pH 4.05 of protein A eluate generated a LRF of 1.68±0.31 and 0.61±0.18, respectively. A dual treatment of X-MuLV by 0.15% Mega-10 in the presence of pH 4.05 protein A eluate (simultaneous low pH and detergent treatment) generated a LRF of 5.50±0.83, which was far greater than the sum of their individual effects. The observed synergistic effect by the dual treatment of Mega-10 and low pH is attributed to the different mechanisms being utilized by the detergent or the low pH treatment to inactivate enveloped viruses. Furthermore, a simultaneous dual treatment of detergent and low pH not only has a synergistic effect on reducing viral infectivity, but also has a synergistic effect on reducing time needed to inactivate enveloped viruses. We observed that a dual treatment in low pH protein A eluate with the presence of a detergent such as Mega-10 or Tween-80 or Tween 20 could reduce the time needed for inactivating X-MuLV to the level below detection limit from 1-2 hours needed by low pH treatment alone to 2.5-10 minutes by the dual treatment. The synergistic effects of simultaneous treatment of low pH and detergent in reducing the time needed to achieve a LRF≥5.0 by a low pH treatment from ≥120 minutes at pH≥3.90 at 16° C. to less than 10 minutes will have a potential utility in retrovirus inactivation during monoclonal antibody manufacturing via continuous processing.

Because of its low cost, less capital investment, more flexibility, more process control, easier to scale up and better product quality, continuous processing has become more common among biopharmaceutical companies. There is an increasing interest for the biopharmaceutical industry to move from operating in batch mode to continuous manufacturing in order to meet the future requirements of the biopharmaceutical industry. The market of biopharmaceuticals, particularly for antibody-based bio-therapeutic products has drastically changed during the last decade as the patents for more than 20 first-generation blockbuster biologics are expiring soon. Therefore, there is a need for cost effective production processes that can flexibly switch productions for different bio-therapeutic products, stable or unstable, at different volumes. A manufacturing process is considered a fully continuous process if it is composed of integrated (physically connected) continuous unit operations with zero or minimal hold volume in between. Currently, almost all unit operations of a standard monoclonal antibody manufacturing are in the continuous processing ready mode except for the low pH viral inactivation step that is currently carried out in a batch process. In general, the eluate pool of the protein A affinity column capture step is adjusted to the desired pH and held in a vessel or a bag for the required inactivation time of 60-120 minutes, depending on the process parameters. Generally, the higher pH, the longer inactivation time is needed and there will be a higher product loss due to the aggregation of antibodies. This represents a challenge in adapting to continuous process. An important consideration when converting current low pH viral inactivation in batch process to continuous process is to ensure the viral inactivation time in the flow mode is as precise and controlled as it is in the batch mode. To accommodate the typical residence time (1-2 hr) for low pH viral inactivation and flow rates of protein A continuous chromatography eluates (50-300 L/hr) as well as a large numbers of elution pools, a very long and narrow pipe is needed for developing a unit operation for continuous low pH viral inactivation. However, it should be noted that such unit operation would generate high back pressure and a wide residence time distribution, causing a drastically decreased of monomers to the formation of aggregates. Currently, a "coiled-flow inverter" (CFI) consisting helix modules and 90 degree bends with a narrow residence time has been proposed to address these problems (Klutz, S., Lobedann, M., Bramsiepe, C., and Schembecker, G., 2016) and is currently at the proof-of-concept stages.

The present embodiments address the technical challenges associated with the conversion of low pH viral inactivation from current batch process to continuous process by replacing existing treatment processes with a simultaneous dual treatment of low pH and detergent to shorten the time needed for viral inactivation. The present embodiments and discoveries remarkably and unexpectedly demonstrate that a dual treatment of low pH protein A eluate with addition of a low concentration of detergent such as Mega-10 or Tween-80 or Tween 20 can reduce the time needed for inactivating retrovirus from 60-120 minutes by low pH treatment to 2.5-10 minutes. Therefore, incorporating a simultaneous dual treatment of low pH and detergent into a continuous monoclonal antibody manufacturing process could drastically reduce the time needed for low pH viral inactivation, thus eliminating the need for a long narrow pipe or CFI to accommodate the extended time needed for low pH viral activation. This could provide improved manufacturing results and yields for antibodies that are labile under lower pH conditions and long holding times. Furthermore, incorporation of simultaneous dual treatment of low pH and detergent in the continuous process will be cost-effective and help eliminate the need for designing and using a costly scale-down model of CFI.

We claim:

1. A virus inactivation method for use in continuous process manufacturing of a biologic, comprising:
   (a) separating an eluate with a biologic and active virus using a column;
   (b) subjecting said eluate with said active virus to an orthogonal treatment of low pH, wherein the pH is from 3 to 4, and a Mega-10 non-ionic detergent, wherein Mega-10 is a N-Methylglucamide, simultaneously to inactivate said virus;
   wherein the time for viral inactivation of the eluate is reduced as compared to the separate treatment time of the eluate using low pH or the Mega-10 non-ionic detergent, the biologic is retained, wherein the virus comprises enveloped viruses, in a family selected from the group consisting of: *Retroviridae, Flaviviridae-, Togaviridae, Coronaviridae, Filoviridae, Rhabdoviridae, Bunyaviridae, Orthomyxoviridae, Paramyxoviridae, Arenaviridae, Hepadnaviridae, Herpesviridae, Baculoviridae and Poxviridae*, and the Mega-10 non-ionic detergent concentration is in the range of from 0.05-1%(w/v).

2. The virus inactivation method as recited in claim 1, wherein the column comprises an affinity column.

3. The virus inactivation method as recited in claim 2, wherein the affinity column comprises a protein A column.

4. The virus inactivation method as recited in claim 1, wherein the biologic comprises a protein.

5. The virus inactivation method as recited in claim 1, wherein the biologic comprises an antibody.

6. The virus inactivation method as recited in claim 1, wherein the biologic comprises an antibody fragment.

7. The virus inactivation method as recited in claim 1, wherein the eluate comprises a biologic of 1 to 100 mg/mL (w/v).

8. The virus inactivation method as recited in claim 1, wherein the virus inactivation time is reduced from 60-120 minutes to 3-4 minutes.

9. The virus inactivation method as recited in claim 1, wherein the retrovirus-virus comprises, X-MuL V.

10. The virus inactivation method as recited in claim 1, wherein the *Herpesviridae* comprises porcine pseudorabies virus (PRV).

11. The virus inactivation method as recited in claim 1, wherein the virus inactivation method takes place in a temperature range of 2-30° C.

* * * * *